US00PP30781P2

(12) United States Plant Patent
Kievit

(10) Patent No.: US PP30,781 P2
(45) Date of Patent: Aug. 6, 2019

(54) ***PHLOX* PLANT NAMED 'BALKAPOPUR'**

(50) Latin Name: *Phlox paniculata*
Varietal Denomination: Balkapopur

(71) Applicant: Ball Horticultural Company, West Chicago, IL (US)

(72) Inventor: Christa Kievit, Hem (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/999,934

(22) Filed: Aug. 31, 2018

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

*Primary Examiner* — Susan McCormick Ewoldt
(74) *Attorney, Agent, or Firm* — Audrey Charles

(57) ABSTRACT

A new and distinct cultivar of *Phlox* plant named 'Balkapopur', characterized by its medium purple-colored flowers, medium green-colored foliage, and moderately vigorous, compact-upright growth habit, is disclosed.

1 Drawing Sheet

Latin name of genus and species of plant claimed: *Phlox paniculata.*

Variety denomination: 'Balkapopur'.

BACKGROUND OF THE INVENTION

The present invention relates to a new and distinct cultivar of *Phlox* plant botanically known as *Phlox paniculata* and hereinafter referred to by the cultivar name 'Balkapopur'.

The new cultivar originated in a controlled breeding program in Hem, the Netherlands during August 2013. The objective of the breeding program was the development of *Phlox* cultivars with attractive flower coloration, increased powdery mildew resistance and a compact growth habit.

The new *Phlox* cultivar is the result of open-pollination within an insect-cage environment. The female (seed) parent of the new cultivar is the proprietary *Phlox paniculata* breeding selection coded D05, not patented, characterized by its medium purple-colored flowers, medium green-colored foliage, and moderately vigorous, compact-upright growth habit. The male (pollen) parent of the new cultivar is one of four proprietary *Phlox paniculata* breeding selections, not coded, not patented, characterized by having different shades of purple-colored flowers, medium green-colored foliage, and moderately vigorous, highly-branched, upright growth habit. The new cultivar was discovered and selected as a single flowering plant within the progeny of the above stated open-pollination during July 2014 in a controlled environment in Hem, the Netherlands.

Asexual reproduction of the new cultivar by terminal stem cuttings since July 2014 in Hem, the Netherlands and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balkapopur' as a new and distinct cultivar of *Phlox* plant:

1. Medium purple-colored flowers;
2. Medium green-colored foliage; and
3. Moderately vigorous, compact-upright growth habit.

Plants of the new cultivar differ from plants of the female parent primarily in having a different shade of flower color and increased branching. Plants of the new cultivar differ from plants of the potential male parents primarily in having a different shade of flower color.

Of the many commercially available *Phlox* cultivars, the most similar in comparison to the new cultivar is Flame Purple 'Barfourteen', U.S. Plant Pat. No. 12,605. However, in side by side comparisons, plants of the new cultivar differ from plants of 'Barfourteen' in at least the following characteristics:

1. Plants of the new cultivar have a flower color that has more purple than plants of 'Barfourteen';
2. Plants of the new cultivar are shorter than plants of 'Barfourteen'; and
3. Plants of the new cultivar have larger diameter flowers than plants of 'Barfourteen'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balkapopur'. The plants were approximately four months old. The plants were grown in one-gallon containers for approximately 11 weeks in a greenhouse in Elburn, Ill. Plants were given two pinches, one at one week before transplant and one two weeks after transplant.

DETAILED BOTANICAL DESCRIPTION

Figure 1:
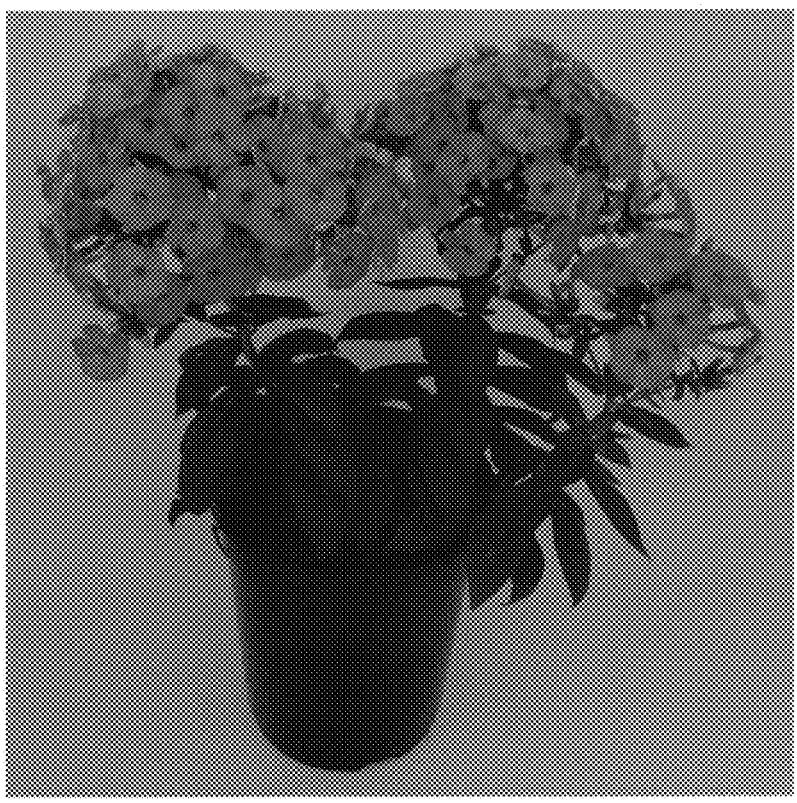
FIG. 1 illustrates a side view of the overall growth and flowering habit of 'Balkapopur'.
Figure 2:
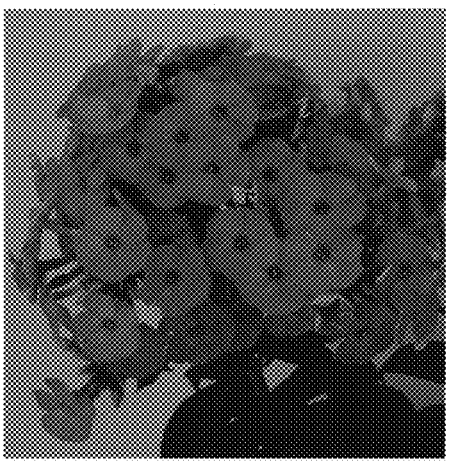
FIG. 2 illustrates a close-up view of an individual inflorescence of 'Balkapopur'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2018 under natural light conditions in West Chicago, Ill.

The following descriptions and measurements describe approximately four-month old plants produced from cuttings from stock plants and grown under conditions comparable to those used in commercial practice. The plants were grown in one-gallon containers for approximately 11 weeks in a greenhouse in Elburn, Ill. Plants were given two pinches, one at one week before transplant and one two weeks after transplant. Greenhouse temperatures were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Phlox paniculata* 'Balkapopur'.

Parentage:

*Female parent*.—Proprietary *Phlox paniculata* breeding selection coded D05, not patented.

*Male parent*.—One of four proprietary *Phlox paniculata* breeding selections, not coded, not patented.

Propagation:

*Type cutting*.—Terminal stem.

*Time to initiate roots*.—Approximately 10 to 12 days.

*Time to produce a rooted cutting*.—Approximately 42 to 49 days.

*Root description*.—Fine to medium thickness, medium density.

*Rooting habit*.—Freely branching, medium density.

Plant description:

*Commercial crop time*.—Approximately 10 to 12 weeks from a rooted cutting to finish in a 15 cm pot.

*Growth habit and general appearance*.—Herbaceous perennial, moderately vigorous, compact-upright growth habit.

*Hardiness*.—USDA Zone 4b (−25° F. to −25° F./−20° C. to −28.9° C.).

*Size*.—Height: Approximately 28.0 cm. Width: Approximately 34.0 cm.

*Branching habit*.—Freely branching, pinching will improve branching.

*Branch*.—Quantity: Approximately 3 basal branches. Shape: Round. Strength: Strong. Length to base of inflorescence: Approximately 14.0 cm. Diameter: Approximately 5.0 mm. Length of central internode: Approximately 1.0 cm. Texture: Glabrous. Color of young stems: 146C. Color of mature stems: 146C, becoming woody 199C with age.

Foliage description:

*General description*.—Quantity of leaves per main branch: Approximately 20. Fragrance: None detected. Form: Simple. Arrangement: Opposite.

*Leaves*.—Shape: Elliptic, slightly carinate. Margin: Entire, minutely ciliate. Apex: Acute. Base: Attenuate. Venation pattern: Pinnate. Length: Approximately 8.5 cm. Width: Approximately 3.2 cm. Texture of upper surface: Sparsely pubescent. Texture of lower surface: Glabrous. Color of upper surface of young and mature foliage: 137A with venation of 145C. Color of lower surface of young and mature foliage: Closest to 191A with venation of 145D.

*Petioles*.—Length: Approximately 2.0 mm. Width: Approximately 3.0 mm. Texture: Moderately pubescent. Color: 145D.

Flowering description:

*Flowering habit*.—'Balkapopur' is freely flowering under outdoor growing conditions with substantially continuous blooming from late spring throughout summer.

*Lastingness of individual flower on the plant*.—Approximately 10 days.

Inflorescence description:

*General description*.—Type: Compound terminal panicle, flowers face upright and outwardly, self-cleaning. Quantity per plant: Approximately 3. Fragrance: Moderately sweet and pleasant. Height of primary: Approximately 10.0 cm. Width of primary: Approximately 13.0 cm. Quantity of fully open flowers per primary inflorescence: Approximately 50. Height of secondary: Approximately 5.5 cm. Width of secondary: 7.5 cm. Quantity of fully open flowers per secondary inflorescence: Approximately 12.

*Peduncle*.—Strength: Strong. Aspect: Primary erect, axillary acute angle to stem. Length of primary: Approximately 3.5 cm. Diameter of primary: Approximately 5.0 mm. Length of axillary: Approximately 3.0 cm to 6.0 cm. Diameter of axillary: Approximately 2.0 mm. Texture: Densely pubescent. Color: 146C.

Flower description:

*Type*.—Single.

*Bud*.—Rate of opening: Generally takes 3 to 4 days for bud to progress from first color to fully open flower.

*Bud just before opening*.—Shape: Oblanceolate. Length: Approximately 1.9 cm. Diameter: Approximately 4.0 mm. Color: 145C with petal portion of NN155D mottled with N88B.

*Corolla*.—Shape: Salverform. Diameter: Approximately 2.7 cm. Depth: Approximately 2.5 cm.

*Petals*.—Quantity: 5 in a single whorl, base fused into a narrow tube. Lobe shape: Obovate. Margin: Entire. Apex: Obtuse. Lobe length: Approximately 1.2 cm. Lobe width: Approximately 1.5 cm. Texture of upper and lower surfaces: Smooth, glabrous. Color of upper surface when first open: NN78B heavily tinted with N81B. Color of lower surface when first open: NN155D mottled with N82B. Color of upper surface when fully open: NN78C tinted with N81B to N81C. Color of lower surface when fully open: NN155D mottled with N82B.

*Corolla tube*.—Length: Approximately 2.1 cm. Diameter at distal end: Approximately 3.0 mm. Diameter at proximal end: Approximately 2.0 mm. Texture of outer surface: Moderately pubescent. Texture of inner surface: Smooth, glabrous with lower 6.0 mm densely pubescent. Color of inner surface: N82A at throat opening transitioning through NN155D to 145D at base. Color of outer surface: NN155D mottled with N82B, 145D at base.

*Calyx*.—Shape: Cupped. Length: Approximately 9.0 mm. Diameter: Approximately 3.0 mm.

*Sepals*.—Quantity per flower: 5, lower half fused. Shape: Lanceolate. Apex: Narrowly apiculate. Length: Approximately 9.0 mm. Width: Approximately 2.0 mm. Texture of outer surface: Sparsely pubescent. Texture of inner surface: Smooth, glabrous. Color of inner surface: 146C with tip of N186A. Color of outer surface: 146D with tip of and central streak of N186A.

*Pedicel*.—Strength: Strong, flexible. Aspect: Primary erect, axillary acute angle to peduncle. Length: Approximately 4.0 mm. Diameter: Approximately 1.0 mm. Texture: Densely pubescent. Color: 146C typically tinted with 187A.

*Reproductive organs*.—Androecium: Stamen quantity: 5 per flower, adnate to corolla tube. Stamen length: Approximately 2.0 cm. Filament length of free portion: Approximately 1.0 mm. Anther shape: Sagittate. Anther length: Approximately 2.0 mm. Anther color: 158B. Pollen amount: Abundant. Pollen color: 155D. Gynoecium: Pistil quantity: 1 per flower. Pistil length: Approximately 1.7 cm. Stigma shape: Cleft, three-parted. Stigma color: 145D. Style length: Approximately 1.5 cm. Style color: 145D. Ovary length: Approximately 2.0 mm. Ovary color: 144A.

Seed and fruit production: Neither seed nor fruit production has been observed.

Disease and pest resistance: Increased resistance to powdery mildew has been observed.

What is claimed is:

1. A new and distinct cultivar of *Phlox* plant named 'Balkapopur', substantially as herein illustrated and described.

* * * * *